United States Patent [19]

Hannon et al.

[11] Patent Number: 4,540,661

[45] Date of Patent: Sep. 10, 1985

[54] COMPOSITION OF MATTER AND PROCESS

[75] Inventors: Betty R. Hannon, Kalamazoo Township, Kalamazoo County; Fritz Reusser, Portage; Lester A. Dolak, Cooper Township, Kalamazoo County; Alexander D. Argoudelis, Portage; Thomas M. Castle, Cooper Township, Kalamazoo County, all of Mich.

[73] Assignee: The Upjohn Company, Kalamazoo, Mich.

[21] Appl. No.: 469,375

[22] Filed: Feb. 24, 1983

[51] Int. Cl.$^3$ .................. C12P 39/00; C12P 13/00; C12N 1/20; C12R 1/05; C12R 1/465

[52] U.S. Cl. ................................. 435/42; 435/128; 435/253; 435/829; 435/886

[58] Field of Search .................. 435/42, 128, 253, 829

[56] References Cited

U.S. PATENT DOCUMENTS 2,635,978  4/1953  Massengale .

FOREIGN PATENT DOCUMENTS 815537  6/1959  United Kingdom .
815538  6/1959  United Kingdom .

OTHER PUBLICATIONS

American Type Culture Collection Catalogue of Strains I, 15th edition, 1982 pp. 221 and 222.

Primary Examiner—Lionel M. Shapiro
Attorney, Agent, or Firm—Roman Saliwanchik; Joan Thierstein; Paul J. Koivuniemi

[57] ABSTRACT

Antibiotic U-66,026 is produced in a fermentation under controlled conditions using the microorganism *Alcaligenes* sp., NRRL B-15269. Enhanced fermentation of titers U-66,026 are obtained when Alcaligenes sp., NRRL B-15269, is cultivated in mixture with *Streptomyces plicatus* strain 395, NRRL 15273.

Antibiotic U-66,026 is a useful antibiotic which has antifungal activity.

6 Claims, 5 Drawing Figures

220 MHz PMR SPECTRUM IN $d_6$-DMSO

220 MHz CMR SPECTRUM AT 30° AND WITH D2O ADDED (IN d6-DMSO TMS)

COMPOSITION OF MATTER AND PROCESS

DESCRIPTION

BACKGROUND OF THE INVENTION

Efforts to develop new and effective antifungal agents are not of recent origin. Such attempts have existed in the antimicrobial art as long as the first recognition of fungal diseases in plants, animals, birds and humans. Though some beneficial antifungal agents are presently available to the public, the need still exists for more effective antifungal agents. Exemplary of prior art work in this antifungal areas are two British patents. British No. 815,538 concerns "N-Nitroso-Hydroxylamines and Fungicidal Agents"; British No. 815,537 concerns "Improvements in the Production of N-Nitroso-N-alkyl- and N-Nitroso-N-Cycloalkyl-Hydroxylamines". This work is somewhat related to the compound produced by the process of the subject invention. The British patents are not concerned with hydroxyl containing compounds other than hydroxycycloaliphatics. On the other hand, the compound produced by the subject invention process is a 1-propanol. This difference is carried into the properties of the compounds.

Another patent exemplifying the prior art is U.S. Pat. No. 2,635,978 which concerns "Salts of N-Nitroso Phenylhydroxyl Amines As Fungicides and Bactericides". Again, there is a relationship in terms of the prior art compounds and the compound produced by the process of the invention.

BRIEF SUMMARY OF THE INVENTION

Antibiotic U-66,026 is producible in a fermentation under controlled conditions using a biologically pure culture of the new microorganism placed in the genus Alcaligenes in the family Achromobacteriaceae. It has been given the culture repository number NRRL B-15269.

Enhancing the fermentation production of U-66,026 is the novel microorganism *Streptomyces plicatus* strain 395. It has been given the culture repository number NRRL 15273.

Antibiotic U-66,026 has been identified as 2-nitrosohydroxylamino-1-propanol.

This compound can be prepared by chemical synthesis as shown in Chart 1.

2-Nitrosohydroxylamino-1-propanol, it analogs, optical isomers, and salts thereof, as disclosed herein, are valuable antifungal agents. Tests have shown that the subject antifungal agent has a broad spectrum of antifungal activity of a standard agar dilution assay. Fungi which are inhibited are as follows:

*Nocardia asteroides*—UC 2052
*Blastomyces dermatitidis*—UC 1466
*Geotrichum sp.*—UC 1207
*Hormodendrum compactum*—UC 1222
*Phialophora verrucosa*—UC 1807
*Cryptococcus neoformans*—UC 4869
*Cryptococcus neoformans*—UC 1139
*Sporotrichum schenckii*—UC 1364
*Monosporium apiospermum*—UC 1248
*Candida albicans*—UC 7163
*Candida albicans*—UC 7164
*Microsporum canis*—UC 1395
*Trichophyton rubrum*—UC 1458
*Trichophyton interdigitale*—UC 1398
*Trichophyton violaceum*—UC 1459
*Trichophyton asteroides*—UC 4775
*Trichophyton mentagrophytes*—UC 4797
*Trichophyton mentagrophytes*—UC 4860

NOTE: "UC" is a registered trademark of The Upjohn Company Culture Collection.

In view of these desirable antifungal results, it is clear that the compounds of this invention are useful as fungicides in animals, birds and man. For this utility, they can be used topically in creams, ointments, sprays and solution, or as a vaginal suppository.

The antifungal formulations and methods of use disclosed in U.S. Pat. No. 2,635,978 can be employed to use the subject compounds as fungicides to treat seeds, plants and fruits. The active fungicides of the subject invention are substituted for the fungicide in the formulations disclosed in U.S. Pat. No. 2,635,978.

For use in animals, the subject compounds can be formulated and used in the same manner as is done for the well-known fungicides nystatin, amphotericin B, griseofulvin, and the like.

DETAILED DESCRIPTION OF THE INVENTION

THE MICROORGANISM

Figure 1:
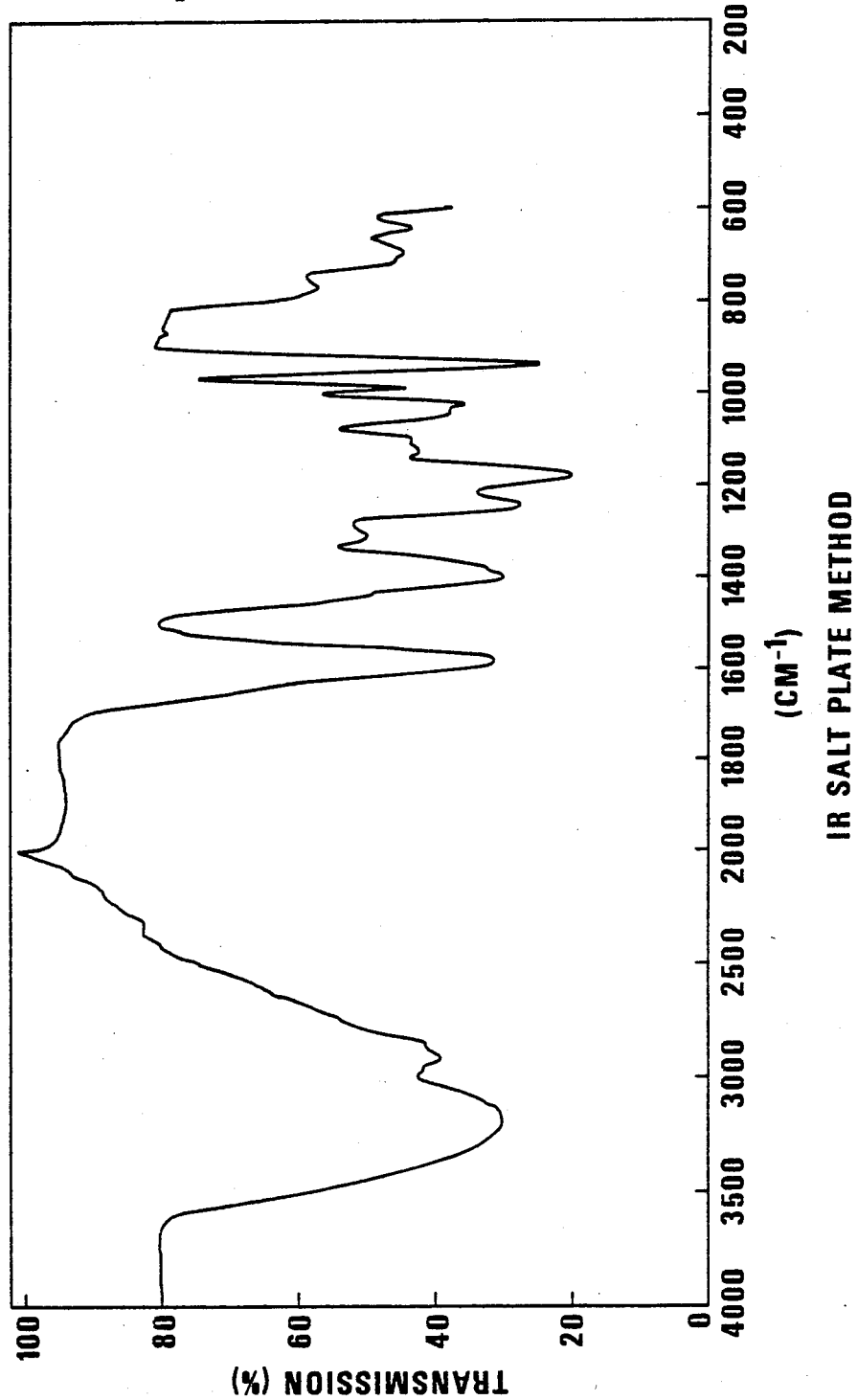
FIG. 1—IR spectrum of U-66,026 in mineral oil mull.
Figure 2:
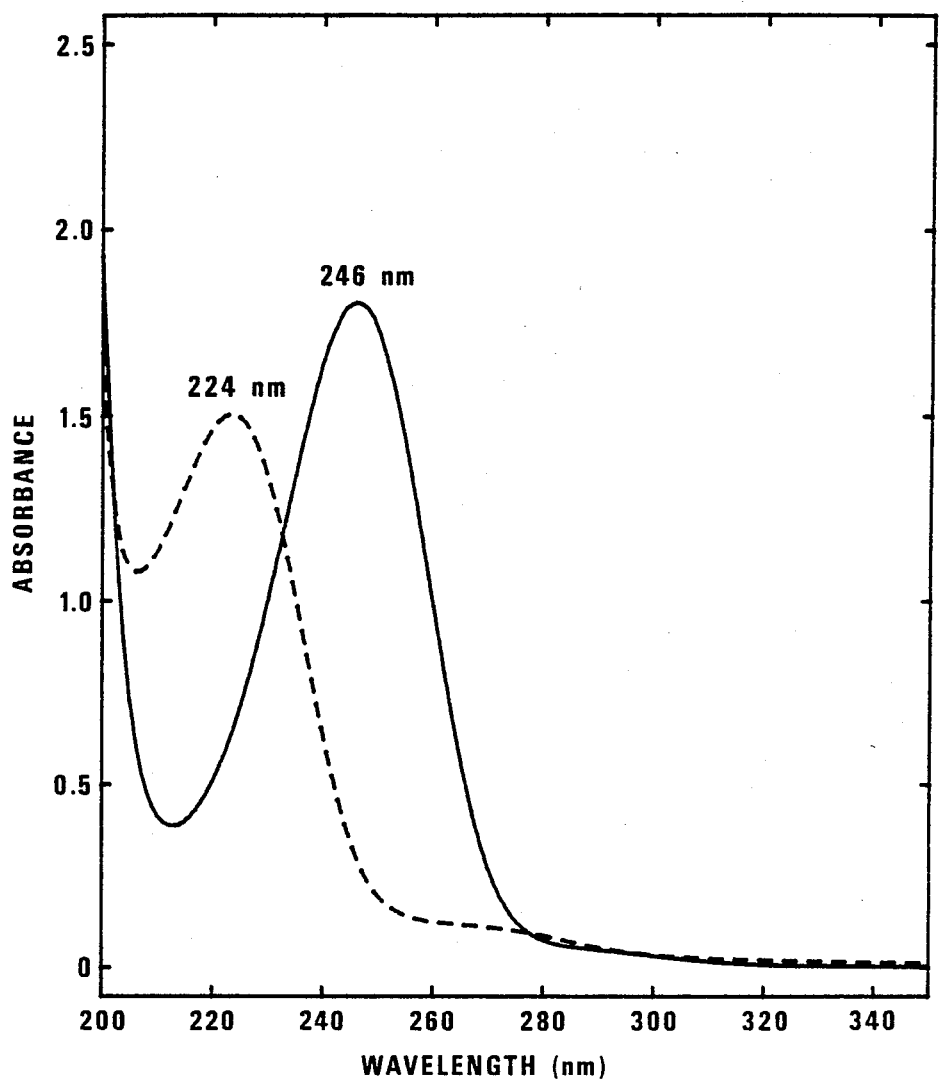
FIG. 2—UV spectrum of U-66,026 at a concentration of 0.0226 mg/ml in water
FIG. 3—CMR spectrum of U-66,026 in $d_6$DMSO/TMS
FIG. 4—PMR spectrum of U-66,026 in $d_6$-DMSO
FIG. 5—CMR spectrum of U-66,026 at 30° with $D_2O$ added (in $d_6$-DMSO/TMS)
Figure 3:
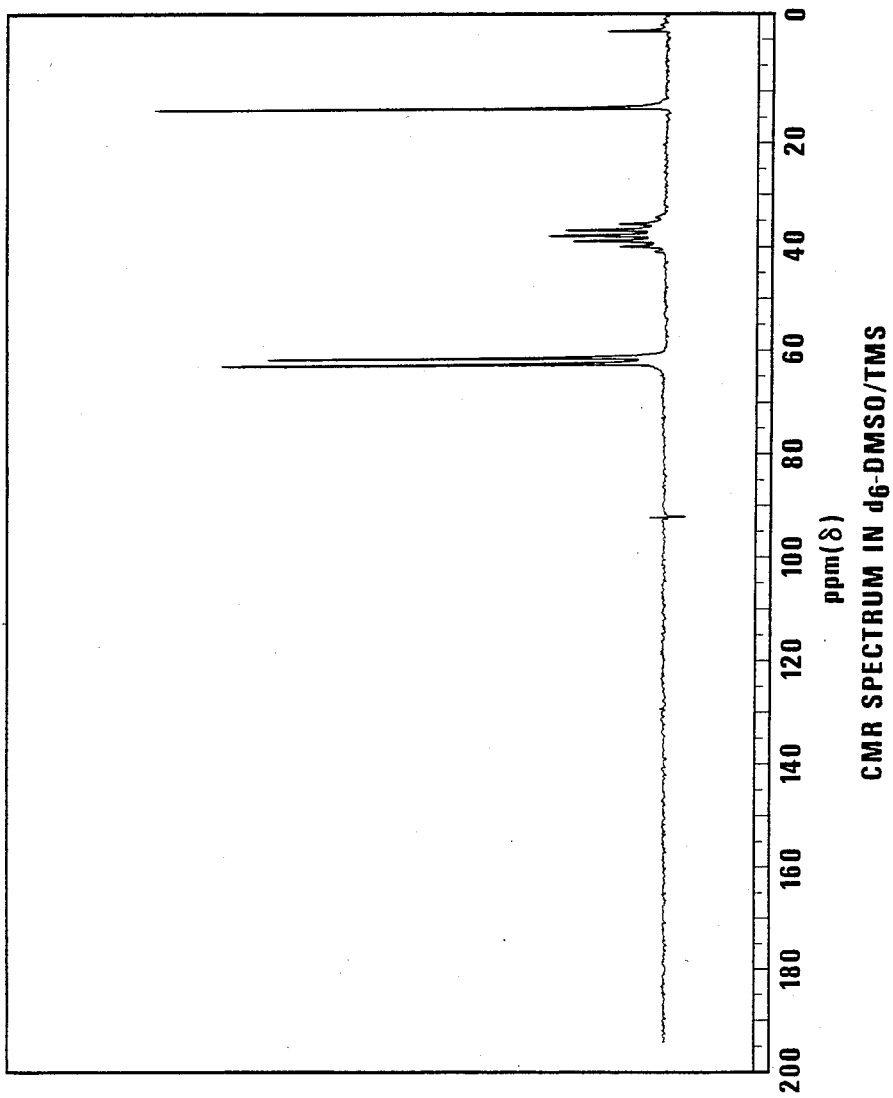
Figure 4:
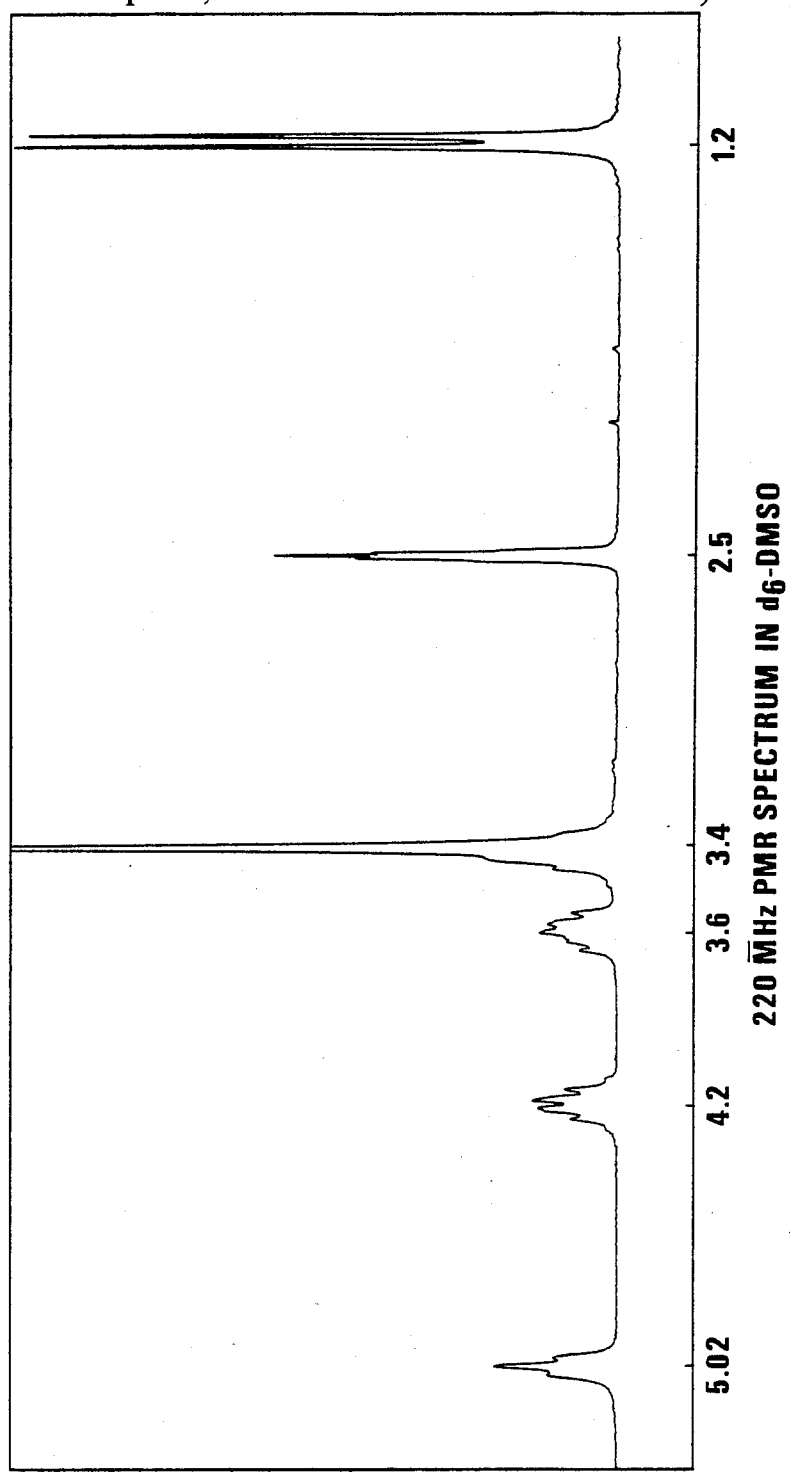
Figure 5:
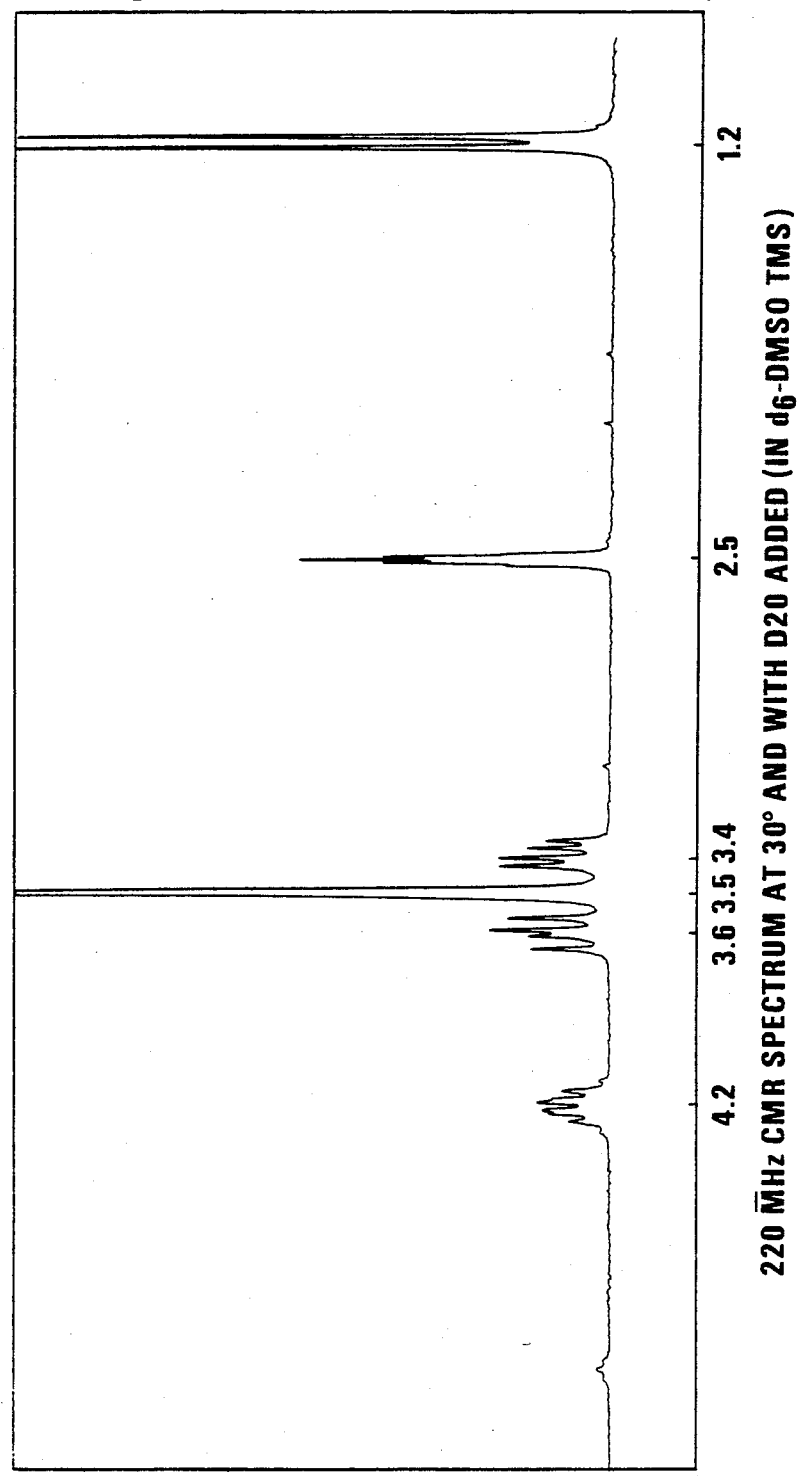

The microorganism used for the production of antibiotic U-66,026 is a biologically pure culture of Alcaligenes sp., NRRL B-15269. Enhancing the fermentation production of U-66,026 is the novel microorganism *Streptomyces plicatus* strain 395, NRRL 15273.

A subculture of these microorganisms can be obtained from the permanent collection of the Northern Regional Research Laboratory, U.S. Department of Agriculture, Peoria, Ill., U.S.A. A viable subculture of NRRL B-15269 was deposited on Jan. 19, 1983; whereas a viable subculture of NRRL 15273 was deposited on Jan. 26, 1983. It should be understood that the availability of these cultures does not constitute a license to practice the invention in derogation of patent rights granted with the subject instrument by governmental action.

Alcaligenes sp., NRRL B-15269.

Morphology. Growth smooth, creamy. Cells short (coccoid rods to rods). Cells larger on Brain Heart Infusion Agar (BHI) after three days at 28 C. than at 37 C. Greater motility is observed in cultures incubated at 28 C. than at 37 C. Cells are gram-negative, nonsporulating, peritrichous and measure 1.29–1.3 $\mu$m in length and 0.36–0.5 $\mu$m in width.

Physiological and Biochemical Characteristics. Broth culture is uniformly turbid at 28 C but not as 37 C. The culture grows in the temperature range of 24 C.–45 C. in 24 hours on BHI Agar. Optimum growth is at 28 C.–45 C. It does not grow at 18 C or 55 C. MacConkey agar is decolorized in 24 hours. Heavy growth is present on BHI agar with 2% rabbit blood. There is no hemolysis. The culture is oxidase and catalase positive. No gas is produced from nitrate. Nitrate reduction to nitrite occurs. There is neither oxidative nor fermentative utilization of glucose. The culture is non-reactive on most biochemical tests in the API and Minitek (BBL) miniaturized test systems. Therefore, it is placed in the group of glucose nonfermenters. It has API Profile 0201004.51 and Minitek Profile 600021. These profiles give a first choice identification of Alcaligenes sp.

Alcaligenes is characterized by its lack of distinctive morphological and biochemical characteristics. This is true of the Upjohn soil isolate which produces antibiotic U-66,026 and which is a non-fermentative, gram-negative, motile rods. The members of the genus Alcaligenes are ubiquitous (Tilton, R. C. 1981. The genus Alcaligenes, p. 856–861. In M. P. Starr, H. Stolp. H. G. Trüper, A. Balows, and H. G. Schlegel (ed.), The Procaryotes. A handbook on habitats, isolation and identification of bacteria. Vol. I. Springer-Verlag, Berlin, Heidelberg, New York). Their speciation is unsatisfactory (Tilton, R. C. 1981, supra; Thornley, M. J. 1968. Properties of Acinetobacter and related genera, p. 29–50. In B. M. Gibbs and D. A. Shapton (ed.), Identification Methods for Microbiologists. Part B. Academic Press, London and New York) except for the well-established *Alcaligenes faecalis* (Holding, A. J., and J. M. Shewan. 1974. Genus Alcaligenes Castellani and Chambers, p. 273–275. In R. E. Buchanan and N. E. Gibbons (ed.), Bergey's Manual of Determinative Bacteriology, 8th ed. The Williams and Wilkins Co., Baltimore; Thornley, M. J. 1968, supra which is the type species (Sherman, V. B. D., V. McGowan, and P. H. A. Sneath. 1980. Approved lists of bacterial names. Int. J. Syst. Bacteriol. 30:225–420). On the basis of the observations made on the morphological and biochemical properties of the new soil isolate the conclusion is made that it is a member of the genus Alcaligenes.

*Streptomyces plicatus* strain 395, NRRL 15273.

Color Characteristics. Aerial mycelium gray-pink to brownish pink. Melanin negative. The color pattern of the culture on Ektachrome is given in Table 1. Reference color characteristics are given in Table 2. The culture may be placed in the Gray (G4) color series of Tresner and Backus (Tresner, H. D., and E. J. Backus. 1963. System of color wheels for streptomycete taxonomy. Appl. Microbiol. 11:335–338).

Microscopic Characteristics. Spore chains are straight to open spiral to spiral. The surface of the spores is smooth. The spores, which are rectangular, vary in length 0.6–1.0 μm and average 0.5 μm in width. Oval bacteria bodies 1.0 μm×0.8 μm with a smooth surface are observed in fields examined for spore chain morphology. The bodies occur singly and in pairs. These have been observed on 12–14 day cover glass preparations examined with the Scanning Electron Microscope.

Growth on Carbon Compounds. See Table 3.

Culture Characteristics—general. See Table 4.

Temperature. The culture grows in the temperature range of 18 C.–37 C. on Bennett's, Czapek's sucrose and Maltose-Tryptone agars. Optimum growth occurs at 24–28 C. The culture does not grow at 45 C.–55 C. Growth is poor at 18 C. and 37 C.

*S. plicatus* strain 395, harbors a bacterium that is not detected by routine culturing or microscopic examination. It is somewhat similar on Ektrachrome to *Streptomyces griseus* ATCC 23345 and *Streptosporangium fragilis* ATCC 31519, but it is readily differentiated from them microscopically. *S. griseus* has straight spore chains, *Streptosporangium fragilis* produces sporangia; the new soil isolate has flexuous to wavy spore chains which terminate in hooks or loops or loose spirals. The culture has a carbon utilization pattern similar to that of several cultures (*S. argentiolus, S. coelicolor, S. endus, S. humidus, S. hygroscopicus, S. plicatus, S. rochei,* and *S. violaceus-ruber*) in Table 17.42f of Part 17. Actinomycetes and Related Organisms in Bergey's Manual, 8th Ed. (Pridham, T. G., and H. D. Tresner. 1974. Part 17. Actinomycetes and related organisms, Family VII. Streptomycetaceae Waksman and Henrici 1943. Genus I. Streptomyces Waksman and Henrici 1943. Table 17.42f of the Gray series. pages 771–772 in Buchanan and Gibbons, eds., Bergey's Manual of Determinative Bacteriology, 8th ed. The Williams and Wilkins Co., Baltimore). The new culture differs in microscopic properties and in color properties from all but *S. plicatus*. A more complete description of this culture is found in Shirling and Gottlieb (Shirling, E. B., and D. Gottlieb. 1966. Cooperative description of type cultures of Streptomyces. IV. Species descriptions from the second, third and fourth studies. Int. J. Syst. Bacteriol. 19:391–512). *S. plicatus* ISP 5319 (NRRL 2428) is reported to have no distinctive pigments on ISP media: yeast malt agar=yeast extract malt extract agar, oatmeal agar, (Inorganic) salts starch agar, and glycerol-asparagine agar. This is in agreement with our observations for the new culture. *S. plicatus* PD 04918 (NRRL 2428) produces Antibiotic C and Antibiotic D. (Parke Davis and Co., British Pat. Specification No. 707,332, April 1954). Production of these antibiotics by the new culture has not been reported: therefore, it is concluded that the bacterium-harboring streptomycete is similar to but different from *S. plicatus*. The new culture is designated *Streptomyces plicatus* strain 395.

The compound of the invention process is produced when the Alcaligenes sp. is grown in an aqueous nutrient medium under submerged aerobic conditions. Higher antibiotic titers results when the Alcaligenes sp. is grown in a mixed culture fermentation with *S. plicatus* strain 395. It is to be understood, also, that for the preparation of limited amounts surface cultures and bottles can be employed. The organisms are grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously.

Production of the compound by the invention process can be effected at any temperature conducive to satisfactory growth of the microorganisms, for example, between about 18° and 40° C., and preferably between about 20° and 28° C. Ordinarily, optimum production of the compound is obtained in about 2 to 15 days. The medium normally remains alkaline during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compound, so long as good growth of the microorganism is obtained.

A variety of procedures can be employed in the isolation and purification of the compound produced by the subject invention from fermentation beers. Isolation can be accomplished using anion exchange resins and by adsorption on non-ionic macroporous resins. Chromatography on silica gel can be used to purify crude preparations of the antibiotic.

The following examples are illustrative of the process of the invention, but are not to be construed as limiting. All percentages are by weight and all solvent mixture proportions are by volume unless otherwise noted.

EXAMPLE 1

Preseed: Shake flasks, seed medium: Cerelose 25 g/l, Pharmamedia 25 g/l. Tap water to 1 liter, pH 7.2 adjusted with KOH. Innoculated with 1 ampule each of NRRL B-15269 and NRRL 15273 frozen seed. Incubate on rotary shaker for 2 days at 28° C.

Seed: 20 liter tank, seed medium same as preseed, 0.5 ml/l SAG-471 antifoam, agitation 400 rpm, air 7 l/min, 5 lb back pressure, incubation temperature 28° C., inoculum size 300 ml preseed. Seed used at end of 2 days.

Frementation: Medium:
Cerelose 10 g/l (clinton)
Yeast extract 1 g/l (Difco)
Polypeptone 10 g/l (Becton, Dickinson & Co.)
Globe Corn Starch 20 g/l (Corn Products)
SAG-471 0.5 g/l (Union Carbide)
Adjust pH to 7.2 with KOH
250 l tank; agitation 280 rpm; air 200 l/min, back pressure 5 lb; temperature 28° C., inoculum 5% seed (12.5 l)

| Typical fermentation in tank | | |
|---|---|---|
| Day | pH | mm zone |
| 1 | 7.9 | — |
| 2 | 6.8 | 34 |
| 3 | — | 34 |
| 4 | 5.1 | 42 |
| 5 | 6.0 | 34 |

Assay:
*Saccharomyces pastorianus*
Agar plate disc diffusion assay. Used deionized water as diluent. The *S. pastorianus* assay denotes the titer of antibiotic U-66,026. The antibiotic is isolated as disclosed in Example 3.

EXAMPLE 2

Upon using only Alcaligenes sp., NRRL B-15269, as inoculum in Example 1, there is obtained a lower titer of antibiotic U-66,026, as given below:

| Day | pH | mm zone |
|---|---|---|
| 2 | 8.9 | 25 |
| 3 | 9.0 | 24 |
| 4 | 9.0 | 24 |
| 5 | 8.5 | 27 |

Assay: sames as Example 1.

EXAMPLE 3

Antibiotic U-66,026 can be obtained from a cultivated fermentation medium by the following procedures:

1. Removal of the bacterial and mycelial growth can be accomplished by centrifugation;
2. The resulting clear supernatant containing antibiotic U-66,026 is adjusted to pH 3.0 and percolated over a bed of Ambersorb XE-348 (Rohm & Haas Co., Philadelphia). The antibiotic is absorbed on the resin and eluted by methanol-0.1N ammonium hydroxide mixture;
3. The bioactive (*S. pastorianus*) methanolic eluate is then passed over Dowex-1 ($OH^-$). Antibiotic U-66,026 is absorbed on the anion exchanger and eluted with 2N ammonium chloride solution;
4. The ammonium chloride is removed by chromatography over Ambersorb XE-348 as described earlier. The antibiotic is obtained as an amorphous, slightly colored (yellow) ammonium salt which is unstable in aqueous acidic solutions. The material is stable in the pH 7.0–10.0 range for at least 72 hours.

Further purification of antibiotic U-66,026 can be done using DEAE-Cellulose chromatography as follows:

DE52 Chromatography

The starting sample (23 gm) is dissolved in 300 ml of water to give a 77 mg/ml solution. A 1:1000 dilution of this solution gives $A_{248} = 1.23$. Therefore, $a = A/c = 16.0$. The 1:1000 dilution gives a 23 mm zone on *S. past.* (100λ per 12.7 mm disc). This implies 2000 BU/ml or 26 BU/mg for this material. One biounit (BU) is that amount of antibiotic which when placed on a 12.7 mm paper assay disc gives a 20 mm zone of inhibition.

A column of DE-52 ($OH^-$) cellulose (Whatman DEAE cellulose) measuring $5 \times 135$ cm (V = 2.656L) is thoroughly washed with deionized water. The 300 ml feed solution is added at the top. Deionized water (1.0 L) is pumped in and then fractions of 50 ml each are collected. A Linear, 24 hr water to 1N $NH_4OH$ gradient (LKB Ultrograd) is started at the first 50 ml fraction. Every 10th fraction is assayed by UV (200–300 nm) and with *S. past.* (100λ/12.7 mm pad). The results are tabulated below.

On the basis of UV alone, tubes 121–163 are pooled to give 2.125 L of a light yellow solution at pH 10.5. A 1:100 dilution gives a 20 mm zone vs. S. past. This implies 100 BU/ml. Lyophilization gives 9.2 gm of a tacky solid. This implies $a = A/c = 19$ and that the specific activity is 22 BU/mg. This is used in the silica gel column step (below).

| THE DE52 COLUMN ASSAYS | | | |
|---|---|---|---|
| Fraction | A, λ max | Dilution | S. past. |
| 30 | 1.48, 275 nm | 1:10 | tr |
| 40 | 0.41, 275 | 1:10 | NZ |
| 50 | no max | 1:10 | NZ |
| 60 | no max | 1:10 | NZ |

-continued

THE DE52 COLUMN ASSAYS

| Fraction | A, λ max | Dilution | S. past. | |
|---|---|---|---|---|
| 70 | no max | 1:10 | NZ | |
| 80 | no max | 1:10 | NZ | |
| 90 | 0.18 sh, 248 | 1:10 | 23 | mm |
| 100 | 0.42 sh, 248 | 1:10 | 28 | |
| 110 | 0.93 sh, 248 | 1:10 | 37 | |
| 120 | 2.96, 248 | 1:10 | 43 | |
| 130 | 0.74, 248 | 1:100 | 46 | |
| 140 | 0.91, 48 | 1:100 | 49 | |
| 150 | 1.26, 248 | 1:100 | 48 | |
| 160 | 0.79, 248 | 1:100 | 46 | |
| 170, 180 | sh only | 1:10 | NZ | |

NOTE:
The 1.0 L forerun and tubes 1–29 were colorless and inactive with no UV absorption. The pump stopped at tube 161 due to a full fraction collector. The abrupt end of antibiotic elution may be due to prolonged absorption on the resin.
NZ = No zone.
tr = trace

Silica Gel Chromatography

The 9.2 gm of solid obtained from DE52 is dissolved in a minimum volume of methanol. This is loaded atop a column of silica gel which measures 5×150 cm (V=3.0 L) which had been slurry-packed in 6:1 $CH_2Cl_2$:MeOH (V/V). The column is eluted isocratically with this solvent at 50 ml/min until a forerun of 3.0 L is collected. At this point, a manual gradient consisting of 5.0 L of the same solvent in the mixing arm and 5.0 L of methanol in the feed arm is initiated. Fractions of 50 ml/tube are then collected and the flow rate is slowed to 10 ml/min. The table below summarizes the assay by UV.

| Fraction | $A_{248}$ | Dilution | Remark |
|---|---|---|---|
| forerun | no max | — | colorless |
| 10–80 | no max | — | colorless |
| 90 | no max (sh) | — | colorless |
| 100 | 1.57 | 1:10 | colorless |
| 110 | 0.98 | 1:100 | colorless |
| 120 | 2.01 | 1:10 | colorless |
| 130 | 2.60 | 1:10 | light yellow |
| 140 | 0.92 | 1:100 | light yellow |
| 150 | 0.54 | 1:100 | light yellow |
| 160 | 2.74 | 1:10 | light yellow |
| 170 | 1.30 | 1:10 | light yellow |
| 180 | sh only | 1:10 | light yellow |

Tubes 96–120 are pooled to give 1.10 L. This is concentrated on a rotary evaporator and dried on a lyophilizer to give 800 mg of solid. Therefore, the concentration (c) is 0.73 mg/ml. A 1:10 dilution gives A=1.99. Therefore, a=A/c=27.3. The pool gives a 41 mm zone vs. S. past. This is sample 70.1.

Tubes 121–161 are pooled to give 2.06 liters. This is concentrated and dried to give 3.5 gm solid (c=1.75 mg/ml). A 1:100 dilution gives A=0.85. Therefore, a=A/c=48.6. The pool gives a 42 mm zone vs. S. past. This is sample 70.2.

Crystallization of Antibiotic U-66,026: White Crystals

All of sample 70.2 is dissolved in methanol and pH 10 water (NH$_4$OH) is used to dilute the solution to 75 ml. This is allowed to stand in a beaker overnight. The solution is warmed and diluted with acetone to a final volume of 350 ml whereupon the solution is cloudy. This is allowed to stand at 5° for 72 hr. Only an oil separates so the acetone is removed on a rotary and the aqueous concentrate is warmed. Acetone is added to a final volume of 750 ml. A seed crystal is added and the solution immediately began to deposit white crystals. After 4 hours of cooling to room temperature the flask is kept at 5° overnight.

1st crop=0.65 gm; m.p. 275°–8° (dec)
2nd crop=0.18 gm; m.p. 273°–5° (dec).

TABLE 1

Color Characteristics* on Ektachrome (1)

| | Deter- | S. plicatus strain 395 | |
|---|---|---|---|
| Agar Medium | mination | Chip | Color |
| Bennett's | S | 232 | light purple-gray |
| | R | 78 | dark yellow-brown |
| Czapek's Sucrose | S | 231 | pale white |
| | R | 92 | pale yellow-white |
| Maltose Tryptone | S | 232 | light purple-gray |
| | R | 78 | dark yellow-brown |
| Peptone-Iron | S | 72 | dark orange-yellow with |
| | | 257 | very deep purple red ring near bottom |
| | R | 72 | dark orange-yellow |
| 0.1% Tyrosine | S | 231 | pale white |
| | R | 92 | pale yellow-white |
| Casein-Starch | S | 232 | light purple-gray (growth light) |
| | R | 33 | brownish pink |

S = surface color
R = reverse color
*Growth on media in tubes photographed after seven days incubation at 28C. Color was determined by comparison with NBS color chips (SP 440. Color: Universal Language and Dictionary of Names. U.S. Government Printing Office, Washington, D.C. 20402 and SRM 2106. ISCC-NBS Centroid Color Charts. Office of Standard Reference Material, Room B311, Chem. Building, National Bureau of Standards, Washington, D.C. 20234).
(1) Dietz, A. 1954. Ektachrome transparencies as aids in actinomycete classification. Ann. N.Y. Acad. Sci. 60:152–154.

TABLE 2

Reference Color Characteristics*

| | Deter- | S. plicatus strain 395 | |
|---|---|---|---|
| Agar Medium | mina-tion | Chip | Color |
| Bennett's | S | 33 | brownish pink |
| | R | 81 | dark grayish yellowish brown |
| | P | 109 | light grayish olive |
| Czapek's Sucrose | S | 33 | brownish pink |
| | R | 33 | brownish pink |
| | P | — | — |
| Maltose-Tryptone | S | 33 | brownish pink |
| | R | 96 | dark olive brown |
| | P | 91 | dark grayish yellow |
| Yeast Extract- | S | 33 | brownish pink |
| Malt Extract | R | 59 | dark brown |
| (ISP-2) | P | 77 | moderate yellowish brown |
| Oatmeal | S | 33 | brownish pink |
| (ISP-3) | R | 90 | grayish yellow |
| | P | 90 | grayish yellow |
| Inorganic Salts | S | 33 | brownish pink |
| Starch | R | 96 | dark olive brown |
| (ISP-4) | P | 93 | yellowish gray |
| Glycerol-Asparagine | S | 9 | pinkish white |
| (ISP-5) | R | 80 | grayish yellowish brown |
| | P | 79 | grayish yellowish brown |

S = Surface color
R = Reverse color
P = Pigment color
*Color determination was made on growth on plates incubated 14 days at 28C. Color was determined by comparison with NBS color chips (SP 440, supra.

TABLE 3

Growth on Carbon Compounds in the Synthetic Medium of Shirling and Gottlieb*

| Synthetic Medium (ISP-9) | S. plicatus strain 395 |
|---|---|
| Negative Control (No carbon cpd.) | ± |
| Positive Control (D-glucose) | + |
| L-arabinose | ++ |

TABLE 3-continued
Growth on Carbon Compounds in the Synthetic Medium of Shirling and Gottlieb*

| Synthetic Medium (ISP-9) | S. plicatus strain 395 |
|---|---|
| Sucrose | − |
| D-xylose | ++ |
| Inositol | ± |
| D-mannitol | ++ |
| D-fructose | ++ |
| Rhamnose | ++ |
| Raffinose | − |
| Cellulose | − |

++ = Strong utilization
+ = Positive utilization
± = Doubtful utilization
− = No utilization
*Shirling, E. B., and D. Gottlieb. 1966. Methods for characterization of Stretomyces species. Int. J. Syst. Bacteriol. 16:313-340.

TABLE 4
Culture Characteristics - General

| Medium | Determination | S. plicatus strain 395 |
|---|---|---|
| Agar | | |
| Peptone-iron | S | center: gray-pink aerial growth edge: tan vegetative growth |
|  | R | maroon under aerial growth pink-tan under vegetative growth |
|  | P | none |
|  | O | melanin negative |
| Calcium malate | S | pale gray-pink |
|  | R | pale yellow |
|  | P | none |
|  | O | malate solubilized around growth |
| Glucose-asparagine | S | pale pink-white |
|  | R | pale yellow-cream |
|  | P | very pale yellow |
| Skim milk | S | very slight trace white |
|  | R | pale tan-orange |
|  | P | none |
|  | O | casein solubilized |
| Tyrosine | S | pale gray-pink |
|  | R | brown |
|  | P | light brown |
|  | O | tyrosine not solubilized |
| Xanthine | S | pale gray-pink |
|  | R | brown |
|  | P | light brown |
|  | O | xanthine not solubilized |
| Nutrient starch | S | pale cream-gray-pink |
|  | R | brown |
|  | P | pale brown |
|  | O | starch solubilized |
| Yeast extract-malt extract | S | fair pale gray |
|  | R | pale yellow-brown |
|  | P | pale yellow |
| Peptone-yeast extract-iron (ISP-6) | S | trace pale gray-pink aerial on maroon vegetative growth |
|  | R | colorless to maroon |
|  | P | pale yellow-tan |
|  | O | melanin negative |
| Tyrosine (ISP-7) | S | pale gray-pink |
|  | R | pale reddish tan; darker at bottom |
|  | P | pale reddish tan |
|  | O | melanin negative |
| Broth | | |
| Synthetic nitrate | S | no growth |
|  | P | none |
|  | O | compact colorless bottom growth nitrates not reduced |
| Nutrient nitrate | S | gray-pink aerial on surface pellide |
|  | P | brown ½; yellow-tan ½ |
|  | O | colorless compact bottom growth nitrates not reduced |
| Litmus milk | S | pale gray aerial growth on brown surface ring |
|  | P | none |
|  | O | litmus reduced slightly at base pH 6.0 |
| Gelatin | | |
| Plain | S | pale gray-pink |
|  | P | brown ⅓; yellow-tan ⅔ |
|  | O | liquefaction ⅓ |
| Nutrient | S | pale gray-pink |
|  | P | brown ⅓; yellow-tan ⅓ |
|  | O | liquefaction ⅓ |

S = Surface (aerial growth unless otherwise noted) color
R = Reverse color
P = Pigment
O = Other characteristics

CHART I $$CH_3CHCH_2 \underset{NO_2}{|} \xrightarrow[\text{Step I}]{H_2/Pd} CH_3CHCH_2OH \underset{NHOH}{|} \xrightarrow[NH_3]{BuONO}$$

2-nitropropanol     Step II $$CH_3CHCH_2OH$$
$$|$$
$$N-N=O$$
$$|$$
$$O^--NH_4^+$$

Step III ↓ CG-120(Ca++)

$$\left( \begin{array}{c} CH_3 \\ \diagdown \\ CH-N \\ \diagup \\ CH_2OH \end{array} \begin{array}{c} N=O \\ \diagdown \\ \diagup \\ O^- \end{array} \right)_2 Ca^{++}$$

Step I

The reduction can also be done with zinc dust and ammonium chloride. If one molar equivalent of oxalic acid is added, the hydroxylamine can be isolated as the stable oxalate salt.

Step II

The nitrosation can also be done with sodium nitrite in hydrochloric acid.

Step III

Any cation exchange resin can be substituted, such as Dowex 50. The form of the resin determines the cation in the final product (e.g. $Mg^{++}$, $Na^+$, $Cu^+$).

We claim:
1. A process for preparing antibiotic 2-nitrosohydroxyl-amino-1-propanol (U-66,026) which comprises cultivating a mixture of Alcaligenes sp., having the identifying characteristics of NRRL B-15269, and *Streptomyces plicatus* strain 395, having the identifying characteristics of NRRL 15273, in an aqueous nutrient medium under aerobic conditions until substantial antibiotic U-66,026 activity is imparted to said medium.

2. A process, according to claim 1, wherein said aqueous nutrient medium contains a source of assimilable carbohydrate and assimilable nitrogen.

3. A process for preparing antibiotic 2-nitrosohydroxyl-amino-1-propanol (U-66,026) which comprises cultivating Alcaligenes sp., having the identifying characteristics of NRRL B-15269 in an aqueous nutrient medium under aerobic conditions until substantial antibiotic U-66,026 activity is imparted to said medium.

4. A biologically pure culture of the microorganism Alcaligenes sp., having the identifying characteristics of NRRL B-15269, said culture being capable of producing the antibiotic 2-nitrosohydroxyl-amino-1-propanol upon fermentation in an aqueous nutrient medium containing assimilable sources of carbon, nitrogen and inorganic substances.

5. A process for enhancing the fermentation production of antibiotic 2-nitrosohydroxyl-amino-1-propanol by Alcaligenes sp., NRRL B-15269, which comprises fermentating said Alcaligenes s. in the presence of *Streptomyces plicatus* strain 395, NRRL 15273.

6. A mixed culture comprising the microorganisms *Streptomyces plicatus* strain 395, having the identifying characteristics of NRRL 15273, and Alcaligenes sp., NRRL B-15269.

* * * * *